United States Patent [19]

Finckh

[11] Patent Number: 5,397,711
[45] Date of Patent: Mar. 14, 1995

[54] DETERMINATION OF AN ANALYTE IN A SAMPLE LIQUID

[75] Inventor: Peter Finckh, Diessen, Germany

[73] Assignee: Boehringer Mannheim GmbH, Mannheim, Germany

[21] Appl. No.: 221,795

[22] Filed: Apr. 1, 1994

[30] Foreign Application Priority Data

Apr. 6, 1993 [DE] Germany .................. 43 11 252.8

[51] Int. Cl.⁶ .............................. G01N 21/75
[52] U.S. Cl. ............................ 436/164; 436/805;
  436/808; 436/810; 435/4; 435/287; 435/296;
  435/804; 435/975; 422/57; 422/61; 422/82.05
[58] Field of Search ................ 422/55, 57, 58, 61,
  422/82.05; 436/164, 166, 805, 807, 808, 810;
  435/4, 287, 291, 296, 804, 975

[56] References Cited

U.S. PATENT DOCUMENTS

| | | | |
|---|---|---|---|
| 4,391,906 | 7/1983 | Bauer | 435/14 |
| 4,673,654 | 6/1987 | Talmage | 436/66 |
| 4,923,680 | 5/1990 | Nelson | 422/58 |
| 4,990,075 | 2/1991 | Wogoman | 422/58 |

FOREIGN PATENT DOCUMENTS

| | | |
|---|---|---|
| 0222700A1 | 5/1987 | European Pat. Off. . |
| 0253581A1 | 1/1988 | European Pat. Off. . |
| 0308232A3 | 3/1989 | European Pat. Off. . |
| 1-227058 | 9/1989 | Japan .............. G01N 31/22 |
| PCT/US92/-02393 | 10/1992 | WIPO . |

*Primary Examiner*—David A. Redding
*Attorney, Agent, or Firm*—Nikaido, Marmelstein, Murray & Oram

[57] ABSTRACT

The invention concerns a method for the determination of an analyte in a sample liquid by a reaction proceeding in several steps which are separated from one another in time and a suitable reaction vessel for this method.

27 Claims, 3 Drawing Sheets

DETERMINATION OF AN ANALYTE IN A SAMPLE LIQUID

DESCRIPTION

The present invention concerns a method for the determination of an analyte in a sample liquid in a homogeneous liquid phase by a reaction proceeding in several steps which are separated from one another in time and a suitable reaction vessel for carrying out this method.

For the specific detection of certain parameters or analytes in clinical diagnostics it is often necessary to allow two or several chemical reactions to proceed in different steps which are separated from one another in time. The reagents required for the second or a further reaction step in this process should not be present in the reaction mixture during the first reaction step. This procedure requires a special chronological segmentation of reaction steps.

In the case of wet-chemical automated analysers such a reaction procedure is ensured in practice by addition of the reagents at different times from different storage bottles (e.g. Hitachi automated analysers).

Other common methods comprise the migration of a sample solution which, if necessary, is diluted or pretreated through various layers or regions of a porous and absorptive test carrier in succession wherein the various layers or regions each contain the various reagents. In this case the chronological separation and control of the reaction is determined by the suction or flow rate of the reaction solution.

Numerous methods and compositions are known from therapeutic galenics which lead to a delayed release of active therapeutic substances at the site of action. One method is characterized in that an outer layer is used which can only be dissolved under very special chemical conditions which are found at the site of action but not at the sites which are previously passed through.

In another method one utilizes so-called tablet bursting agents. In this case the inside of a tablet is composed of a material capable of swelling which is surrounded by a substantially impervious but water-permeable covering. After a certain time the inside of the tablet has taken up so much water that the swelling pressure bursts the coating and then the active substance contained in the interior is released. However, due to the occurrence of larger insoluble fragments, this principle is unsuitable in a method for the determination of an analyte in a sample solution.

In a third method, the active substance is surrounded by an insoluble but porous substance which strongly impedes diffusion i.e. a microscopic net-work. In this way the release of the active substance contained therein is not prevented but is only considerably delayed to a greater or lesser extent which leads to a uniform slow release of active substance over long time periods. Since large insoluble components occur in this method and a constant but very low release rate of the active substance is found, this method can also not be used to determine an analyte in a sample liquid by a reaction proceeding in several chronologically separate steps.

In the prior art it is known that a considerable number of water-soluble polymers can dissolve at a greater or lesser rate in water depending on their chain length and the number of polar side groups. Although the polymers finally dissolve completely at a given water temperature and stirring efficiency, time periods are necessary for this which, however, differ considerably. Examples of such water-soluble polymers are polyvinylalcohols, polyvinylpyrrolidones, polyacrylic acids and others. A filter system is described in EP-A-0 308 232 which has a membrane impregnated with a water-soluble polymer for the purpose of delaying the water front.

U.S. Pat. No. 4,673 654 discloses the coating of a reagent for a peroxidase test with a water-soluble polymer on an inert water-soluble material together with a second reagent in order to keep the two reagents separate from one another until they are used in the test. The possibility of a sequential release of both reagents is not disclosed.

EP-B-0 253 581 discloses an analytical element for the determination of an analyte in an aqueous liquid comprising a first reagent zone with a carrier and a first biologically active material and a second reagent zone with a second biologically active material which can interact with the first biologically active material characterized in that the first and second reagent zones are located in a single layer in the element and that the second reagent zone is water-soluble and contains a polymeric material which is naturally soluble in water. The purpose of this element is to keep two reagents separate from one another until the test carrier is used in order to avoid a reaction with one another. On addition of an aqueous sample liquid the polymer dissolves and the second reagent is available. In this element the rapid release of the second reagent from the water soluble polymer is described as being advantageous. A sequential release of the two reagents at particular times is in contrast not disclosed. The construction of the test carrier in several separate zones is only for purposes of storage stability. Those polymers are preferably used which dissolve within less than 120 seconds after contact with the sample.

Use of organic solvents for applying biochemical reagents to test strips for diagnostic tests is also known. U.S. Pat. No. 4,391,906 describes the use of an impregnation solution in the production of a test strip for glucose which, among others, contains THF as an organic solvent as well as an ethanolic solution of polyvinylpyrrolidone. The purpose of the organic solvent is presumably to increase the solubility of dye components in the impregnation solution or to improve the drying.

The production of a test strip is described in U.S. Pat. No. 455,640 which is sequentially immersed in various imgregnation solutions wherein an intermediate drying is carried out in order to prevent an intimate mixing of the reagents of the various impregnation solutions until the intended use. One of the impregnation solutions can be produced in an organic solvent or it can be a suspension of an organic and aqueous phase in order to prevent re-dissolving of the reagents of the first impregnation solution during treatment with the second impregnation solution.

However, the prior art mentioned above has considerable disadvantages. Thus the known ready-to-use test elements to which no further reagent has to be added apart from the sample liquid, which is pre-diluted if necessary, do not allow control of several reaction steps. In a chromatographic method of determination in which the reaction solution migrates through various reaction zones in sequence, an absorptive material is required as an essential element which is highly structured and therefore has to be impregnated in a complicated manner with the various reagents requiring a very complicated production process. Even the multi-layer test elements in which the solution migrates through different layers in succession are very complex and thus complicated to produce.

An arrangement in which a reagent is already completely present in a cuvette-type of vessel but which allows a reaction to be carried out in a homogeneous liquid phase which proceeds in several chronologically separate steps is not known up to now. An object of the present invention was therefore to enable a process for the determination of an analyte in a sample liquid by a reaction proceeding in several steps which are separated from one another in time in which the disadvantages of the prior art are at least partially eliminated. In particular a method should be provided in which the reaction can be carried out in a homogeneous liquid phase thereby avoiding the use of an absorptive carrier with the aforementioned disadvantages.

The object according to the invention is achieved by a method for the determination of an analyte in a sample liquid by a reaction proceeding in several steps which are separated from one another in time which is characterized in that the sample liquid containing the analyte is added to a reaction vessel which contains at least two reagents required to carry out the determination reaction in a form which is readily soluble in the sample liquid and spatially separated from one another wherein a first reagent intended for the first reaction step is in a form which is soluble without delay in the sample liquid while a second reagent intended for the second reaction step and, if desired, further reagents are separated from one another and from the first reagent and are protected from an immediate contact with the sample liquid by protective layers wherein the protective layers are designed in such a way that they enable delayed contact between the sample liquid containing the analyte and the reagent located under the respective protective layer so that a reaction of the analyte with the reagents can take place in several steps which are separated from one another in time and so that the analyte can be determined after completion of the reaction in a homogeneous liquid phase.

The method according to the invention takes place in a reaction vessel which contains all reagents necessary for the specific test in a dry form. The reaction vessel is preferably a test carrier of the cuvette type which should preferably have at least two optically transparent sides to carry out an optical determination of the analyte. The reaction vessel is preferably designed to receive 10 $\mu$l to 5 ml sample liquid and particularly preferably 20 $\mu$l to 2 ml sample liquid.

The method according to the invention enables a two step or multiple step reaction to be carried out in chronologically-separate partial reactions. In this process a second (or a further) reagent is withheld from the reaction solution during a certain period of time since otherwise an interference of the respective preceding partial reaction would occur. Subsequently the second (or further) reagent is released into the liquid reaction volume at a desired time in order to start the second (or further) reaction step. In this process it is expedient that the design of the protective layers or/and the procedure enables a reproducible and definable delay in contact between the reagent located under a protective layer with the sample liquid.

The determination of the analyte in the method according to the invention is carried out in a homogeneous liquid phase i.e. the dissolved reagents and the sample liquid form a uniform reaction volume which otherwise only perhaps contains regions of the protective layers which have not yet completely dissolved. In contrast to the prior art, the liquid is not located in the network fibres of an absorptive carrier material.

The production of a suitable reaction vessel for the method according to the invention is preferably carried out by firstly applying a reagent to part of the inner surface of the reaction vessel and drying it. Then this partial surface is coated with a protective layer. Further reagents can if desired be applied to the inner surface of the reaction vessel in a corresponding manner, dried and coated with further protective layers. In the last step the reagent of the first reaction step is preferably applied to the inner surface of the reaction vessel and dried. This reagent does not have to be coated with a protective layer and is therefore in a form which is immediately soluble in the sample liquid.

When several reagents coated with protective layers are used, the individual reagents can be arranged one on top of the other on the same part of the inner side of the vessel (and are separated from one another by a protective layer) or each is located on different parts of the inner surface of the vessel. In the latter case it is necessary that the reagents are protected from contact with the sample liquid by different protective layers in which case the individual protective layers then have to be designed in such a way that they enable contact of the individual reagents with the sample liquid at the time intended for each of them. For this purpose the protective layers can for example be composed of different materials or on the other hand it is also possible that the protective layers are composed of the same material and only differ in their thickness.

In a particularly preferred embodiment of the method according to the invention the protective layers are designed in such a way that they can be made permeable to the sample liquid by the action of the sample liquid or/and by the action of external physical/chemical agents.

Thus for example it is possible that the protective layers can already be made permeable to the sample liquid by action of this alone. Such protective layers preferably contain a water-soluble polymer. Examples of suitable water-soluble polymers are modified cellulose (e.g. carboxymethylcellulose, carboxyethylcellulose, carboxypropylcellulose, hydroxyethylcellulose, hydroxypropylcellulose), gelatin, polyvinylalcohols, polyvinylpyrrolidones, polyacrylamides, polyacrylic acids or mixtures thereof. Particularly preferred polymers are polyvinylpyrrolidone and polyvinylalcohol.

The thickness of the protective layers when using water-soluble polymers depends on the required retardation period, the thickness of the reagent layer and the water-solubility of the polymer. The thickness of the protective layers is usually in the range of 0.1 $\mu$m to 500 $\mu$m.

In a further embodiment of the method according to the invention the protective layers are designed in such a way that they can only be made permeable by the additional effect of external physical-chemical agents. Examples of such external physical-chemical agents are for instance the use of heat or/and radiation. In this embodiment it is preferred that the protective layer contains a photolabile or/and thermolabile polymer.

Examples of such photolabile or/and thermolabile polymers are positive photoresists which are well-known from the production technology for electronic components (see for example Henkes, "Photochemische Verfahren in der Technik", "Die Umschau" 1985, Vol 2; Steppan et al., "Angew. Chem." 94 (1982), 471–564; Shirai et al., Chemistry Express 3 (1988), 439–443; Shirai et al., Makromol. Chem. 190 (1989), 2099–2107 and Ito and Willson, Polymer Eng. a. Sci. 23, (1983), 1012–1017). However, well-known photoresists of the prior art are often only of limited use for the method according to the invention since some of the polymer components are only water-soluble under extreme pH conditions or only have a low light yield.

Examples of photolabile polymers which are particularly suitable for the method according to the invention are triazines or pentazadiene polymers.

Such polymers can for example be obtained by a process in which a bifunctional aromatic or heteroaromatic amino compound is converted by diazotization into a corresponding bis-diazonium salt and this is subsequently reacted with a compound containing amino groups in a polycondensation reaction to produce a polymer. Bis(aminoaryl) compounds and preferably bis(aminoaryl) compounds of the general formula (III) can for example be used as bifunctional aromatic or heteroaromatic amino compounds

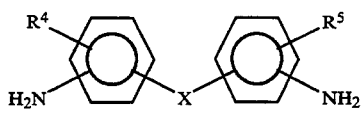   (III)

in which
X denotes a chemical bond, O, S, S—S, SO, $SO_2$, CO, CO—NH, CS, N=N, NH, N(alkyl), Y, COO, $SO_2$—NH, NH—Y—NH, NH—CO—NH, NH—$SO_2$—NH or a saturated or unsaturated hydrocarbon group, $R^4$ and $R^5$ are the same or different, represent one or several substituents on the aromatic ring and each denotes H, $C_{1-4}$ alkyl, $C_{1-4}$ alkoxy, Y, CN, N(alkyl)$_2$, halogen, N=N—Y, thioether, —OY, $SO_3$, $CO_2H$ or their salts and Y denotes an aromatic or non-aromatic cyclic hydrocarbon group which is substituted if desired. Specific examples of such compounds are for instance bis-(4-aminophenyl)-ether, 3,3'-dimethoxybenzidine, 4,4'-diaminobenzanilide, 4,4'-diaminostilbene, 4,4'-diaminostilbene-2,2'-disulfonic acid or bis-(4-aminophenyl)-amine and also monoaromatic or heteroaromatic bifunctional amino compounds. The following are preferably used as the compound containing amino groups:

(a) a bifunctional primary or secondary amine of the general formula (I)

$R^1$—NH—Z—NH—$R^2$   (I), in which Z represents a non-aromatic hydrocarbon group which is substituted if desired or a polymeric residue, $R^1$ and $R^2$ are the same or different and each represents hydrogen, an aliphatic, unsaturated or/and aromatic hydrocarbon group which is substituted if desired or a polymeric residue, or/and (b) a primary amine of the general formula (II)

$H_2N$—$R^3$   (II), in which $R^3$ represents hydrogen, an aliphatic, unsaturated or/and aromatic hydrocarbon group which is substituted if desired or a polymeric residue.

If a bifunctional primary or secondary amine is used as the compound containing amino groups then one can obtain a triazene polymer when the reaction is carried out under appropriate conditions. If ammonia or a primary amine is used as the compound containing amino groups, one can obtain pentazadiene polymers by the polycondensation when suitable reaction conditions are chosen.

Examples of preferred compounds containing amino groups are N,N'-dimethylaminohexamethylenediamine, 2,3,5,6-tetramethyl-p-phenylenediamine, N,N'-dimethylaminoethyldiamine or 2,4,6-trimethyl-m-phenylenediamine.

In this connection it is also possible to use aminofunctional polymers as the compounds containing amino groups. Preferred examples of suitable polymers include amino-functional polyethylenes, poly(allyl)amines, polyethers, polyethylenimines, polysaccharides or polypeptides. Amino-terminal polyethylene oxides, polypropylene oxides or poly-(ethylenepropylene) oxides are particularly preferred.

Triazene or pentazadiene polymers can also for example be prepared by a process in which a monofunctional aromatic or heteroaromatic compound is converted by diazotization into a corresponding mono-diazonium salt and this is subsequently reacted with an aminofunctional polymer in a polycondensation reaction.

The solubility properties of the polymers in an aqueous medium can be modified by reacting the amino groups of the polymers with mono-diazonium salts in such a way that a soluble polymer (having free amino groups) becomes insoluble after partial or complete reaction with a diazonium salt and is thus suitable for the production of protective layers. When the triazene or pentazadiene group is subsequently cleaved by exposure to light, the polymer can again go into solution thus dissolving the protective layer.

Examples of monofunctional aromatic or heteroaromatic amino compounds are aniline or anilines substituted with one or several substituents on the benzene ring, e.g. 3,4,5-trimethoxyaniline or corresponding substances. Preferred examples of amino-functional polymers are for example the aforementioned polyethylenes, poly(allyl)amines, polyethers, polyethylenimines, polysaccharides or polypeptides containing amino groups, in particular amino-terminal poly-ethylenepolypropylene oxides, or poly(ethylene-propylene) oxides.

When protective layers of photolabile polymers are used, one reagent is preferably applied to part of the inner surface of a reaction vessel, preferably a cuvette type of vessel, and dried. Afterwards this partial area and thus also the reagent is coated with a suitable positive photoresist. In this manner one obtains a water-resistant protective layer which, after sufficient exposure to radiation of a suitable wavelength becomes water-soluble and dissolves in water without turbid residues. The reagent located under this is thereby made accessible to the sample liquid and is dissolved. A particular advantage of this arrangement is that the pre-reaction time can be varied very simply within wide limits independently of material properties or complex test conditions since the test carrier has to be merely illuminated with a lamp at the desired starting time in a second partial reaction. The reagent which immediately comes into contact with the sample liquid is applied to the other partial areas of the reaction vessel and dried. A further advantage of this embodiment is that when the sample liquid is mixed with the first reagent there is no danger of a premature dissolution of the protective layer and thus of possible contact of the sample liquid with the second reagent since the protective layer is completely water-insoluble until exposure to light. If desired a further closed intermediate layer which contains no specific reagent can be positioned between the base layer containing the second reagent on the reaction vessel and the protective layer made of positive photoresist.

In both embodiments polymers are particularly preferred whose dissolution kinetics are not linear as is usually the case, but have a sigmoidal character since they promote the retaining effect of the protective layer at the start of the dissolution process but then produce a more rapid dissolution of the protective layer at the end of the dissolution process.

Surprisingly the method according to the invention allows attainment of highly reproducible release kinetics of reagents covered by a protective layer. The time interval during which the reagent located under the protective layer is available can be exactly determined in a first preferred embodiment (water-soluble polymers) on the one hand by the layer thickness and on the other hand by the selected polymer and in a second preferred embodiment (positive photoresist) by the time of the exposure.

The method according to the invention is particularly preferably combined with a specific switching on or off of a mixing agent. In this case the sample liquid, after being added to the reaction vessel, is mixed with a mixing agent until the first reagent is intimately mixed with the sample, the mixing agent is then switched off until the time at which a release of the second reagent is desired and subsequently the mixing agent is again switched on until the second reagent has been adequately mixed. If desired this procedure can be carried out in an analogous manner for further reagents that are located under further protective layers. A preferred mixing agent especially for reaction volumes of <1 ml is ultrasound. In this case sound generators can for example be used which are firmly attached to the vessel wall (see e.g. U.S. Pat. No. 4,930,898 or EP-A-0 052 322). In addition the mixing can also be achieved by stirrers immersed in the liquid (magnetic stirring bars, stirring paddles), by shaking the vessel or blowing it with a stream of air (see e.g. U.S. Pat. No. 4,815,978).

Use of a mixing agent enables for example the time interval of the first reaction step to be varied within wide limits when using water-soluble polymers since in a macroscopically resting liquid only diffusion contributes to the dissolution and mixing of the protective film of water-soluble polymer which is partially dissolved on the surface. This diffusion is only very slight and therefore relatively ineffective due to the high viscosity of the polymer solution at the high concentration which is inevitably present at the surface of the film. The high viscosity of the film surface which has just started to dissolve more or less protects the underlying film from further rapid dissolution. However, during this period the film swells by taking up water so that in the subsequent mixing interval it can be much more rapidly dissolved and homogeneously mixed. This allows a particularly advantageous much steeper concentration step to be achieved for the contact of the second reaction partner with the sample liquid. This is then particularly advantageous when the precision of the starting time of the second reaction step contributes to the precision of the analytical result which is for example the case in pseudo end-point tests.

Even when the method according to the invention is carried out with thermolabile or/and photolabile protective layers it may be preferable to use a mixing agent.

When protective layers are used which contain polymeric materials, the protective layers are preferably made permeable to the sample liquid by an at least partial dissolution. It is particularly preferred that an essentially complete dissolution of the protective layers takes place. The time required for a dissolution of the protective layers leading to a release of reagent is preferably in the range of 10 seconds to 1 hour.

In order to carry out the determination of the analyte it is additionally in general expedient that one of the reagents or the sample liquid contains an indicator substance which enables a determination of the analyte. The determination of the analyte is preferably achieved using optical methods (e.g. spectrometrically). For this it is preferable to use a suitable cuvette type of reaction vessel (e.g. a micro vessel with a diameter of ca. 5 mm and height of 2–3 mm) with at least 2 optically transparent (i.e. suitable for carrying out an optical determination) sides. It is, however, also possible to use a reaction vessel with only one optically transparent side, if the measurement is for example carried out from above through the meniscus of the liquid and bottom of the vessel.

The present invention also concerns a reaction vessel for the determination of an analyte present in a sample liquid by a reaction proceeding in several steps which are separated from one another in time characterized in that it contains at least two reagents required to carry out the determination reaction that are in a form which is readily soluble in the sample liquid and are spatially separated from one another, wherein a first reagent intended for the first reaction step is in a form which is soluble without delay in the sample liquid, while a second reagent intended for the second reaction step and if desired further reagents are separated from one another and from the first reagent and are protected from an immediate contact with the sample liquid by protective layers wherein the protective layers are designed in such a way that they enable a time-delayed contact between the sample liquid containing the analyte and the reagent located under the respective protective layer so that a reaction of the analyte with the reagents can take place in several steps which are separated from one another in time.

The protective layers in the reaction vessel are preferably designed in such a way that they can be made permeable to the sample liquid by action of the sample liquid or/and by action of external physical/chemical agents. Detailed designs of reaction vessels according to the invention have been elucidated in connection with the description of the process.

The application of reagents and protective layers to the inner side of the reaction vessel according to the invention can be carried out by various methods, for example by dropwise addition by means of a pipette, printing with various printing methods, coating using doctor blades and also pouring.

Since the reagents used have to be soluble in the aqueous sample liquid, it is particularly preferable (even if not absolutely necessary) that a polymer forming the protective layer is applied from an organic solution in which the reagent located under it is not itself soluble. This prevents the reagent from being partially dissolved by application of the protective layer and from being partially mixed into the lower region of the protective layer which would lead to a less clear-cut release step for the reagent.

BRIEF DESCRIPTION OF THE DRAWING

It is intended to further elucidate the invention by the following examples and FIGS. 1-5.

EXAMPLE 1

Dissolution Kinetics of Different Water-Soluble Polymers

A round film spot was prepared on the bottom of a commercial semimicro absorption cuvette by dropwise addition and subsequent drying of an aqueous solution of the respective water-soluble polymers which contained 0.2% of a dye (amaranth) as an indicator. After drying this film, 500 μl water was added and continuously mixed using a spatula stirrer immersed from above. The absorbance was registered concurrently as a function of time at a suitable wavelength for the dye (522 nm), i.e. the concentration of dye in the solution which was originally present in the film was used as an indicator for the dissolution of the film.

The experiment was carried out with different polyvinylpyrrolidone (PVP) and polyvinylalcohol (PVA) polymers. The result is shown in FIG. 1.

Figure 1:
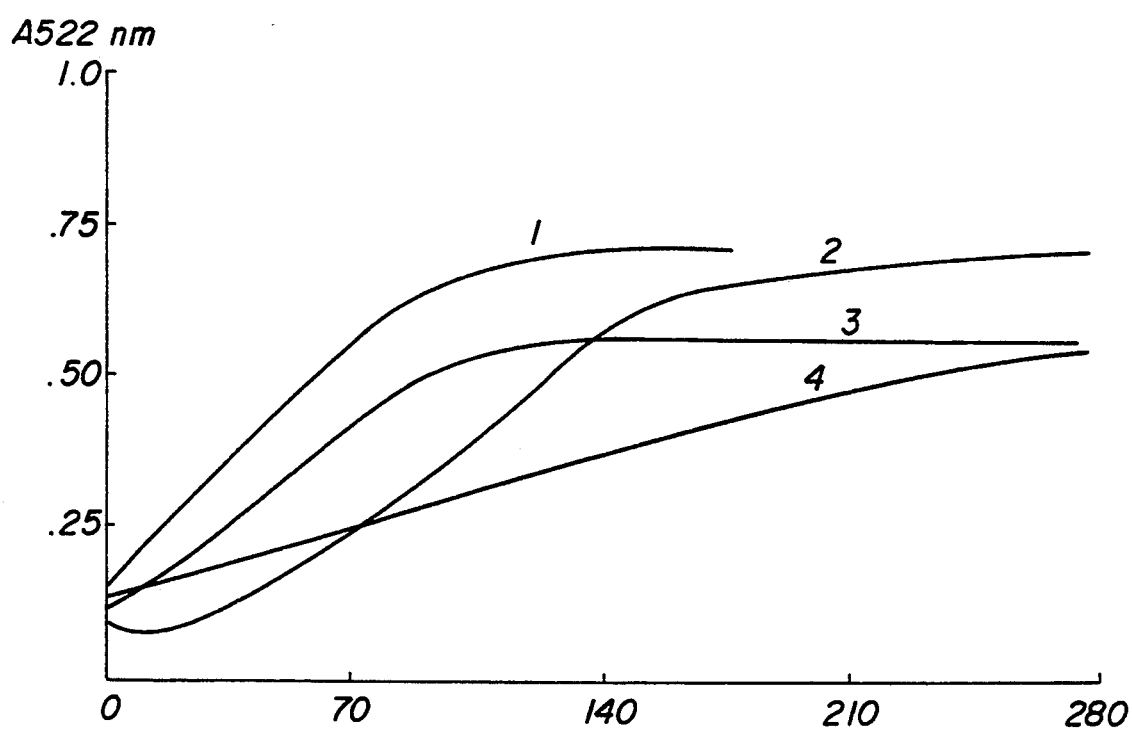
FIG. 1 shows the dissolution kinetics of water-soluble polyvinylpyrrolidone and polyvinylalcohol polymers.

It can be seen from FIG. 1 that the retardation time until complete release can be varied within wide limits by selecting different polymers. The sigmoidal form of the dissolution curve for the polyvinylpyrrolidone PVP 360 is particularly significant (curve 2).

Experimental Conditions

Concentration of polymers: 4% PVP or 5% PVA
dye: 0.2% amaranth
drop volume: 5 μl for PVP or 3 μl for PVA
aqueous solution: 0.1 mol/l NaPO$_4$ buffer pH 7
wavelength: 522 nm
Curve 1: PVP 10 (Sigma 10 S/0001)
Curve 2: PVP 360 (Sigma 28 F/0009)
Curve 3: PVA 3-88 (Hoechst Mowiol 3-88)
Curve 4: PVA 8-88 (Hoechst Mowiol 8-88)

EXAMPLE 2

Release Kinetics of an Overlaid Dye

An area of 2×8 mm on a film was covered with solution 1 (5% PVA 4-88 (Hoechst Mowiol 4-88), 1% polyethylene glycol (PEG) 400, 0.1% Triton X-100, 1% patent blue in 100 mmol/l sodium phosphate buffer pH 7). This solution 1 formed a film which after drying was almost spontaneously soluble in water. Subsequently a uniform layer of 200 μm thickness of solution 2 (20% PVP 360, 0.1% PEG 400 in cyclohexanol) was applied to a large area of the film using a hand-held doctor blade, which after drying again forms a uniform film coating which has a delaying effect on the dissolution of the dye in the lower layer. Areas of 4×10 mm were punched out of the foil and placed at the bottom of a semimicrocuvette. The experimental procedure was then analogous to example 1, i.e. the dye concentration in solution was measured photometrically while stirring continuously. The measuring wavelength was 640 nm.

Figure 2:
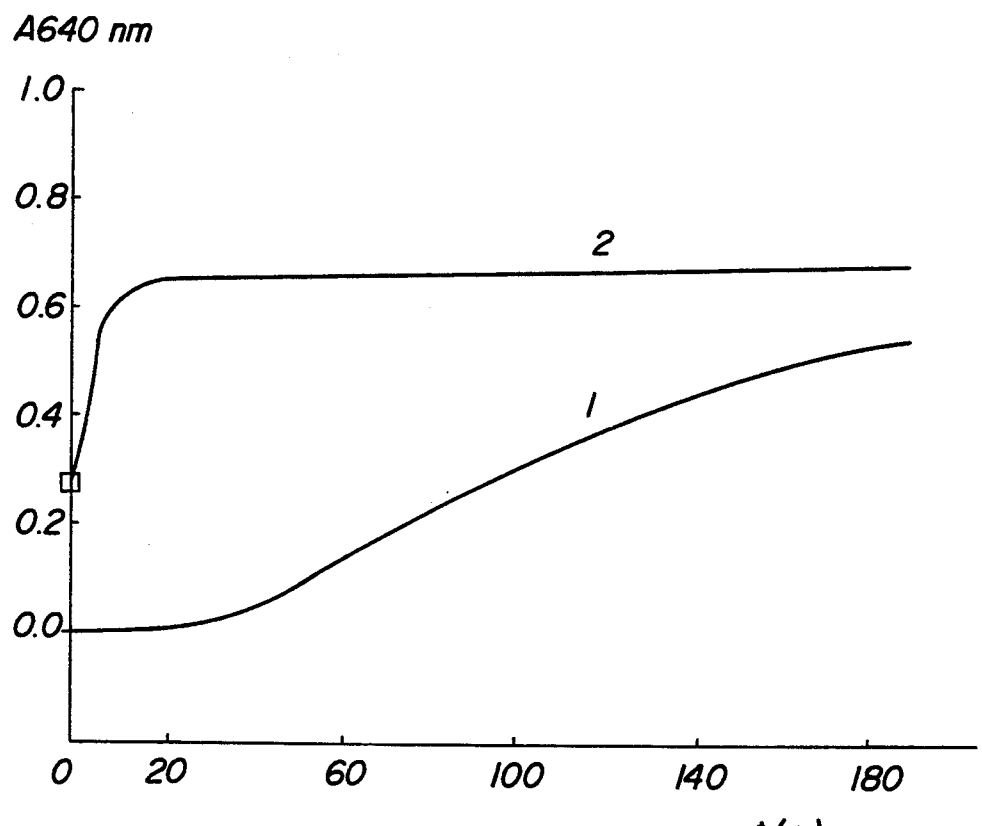
FIG. 2 shows the release kinetics of a dye overlaid with a water-soluble polymer.

The result of this experiment is shown in FIG. 2. Curve 1 shows the experiment described above which was repeated three times. Curve 2 shows in comparison the result of the experiment when the covering layer of solution 2 is omitted. In this case the dissolution then takes place practically spontaneously. The increase in absorbance at the start of the experiment in curve 2 is essentially only due to the time required to mix the cuvette volume once.

EXAMPLE 3

Influence of the thickness of the protective layer on the dissolution kinetics

Figure 3:
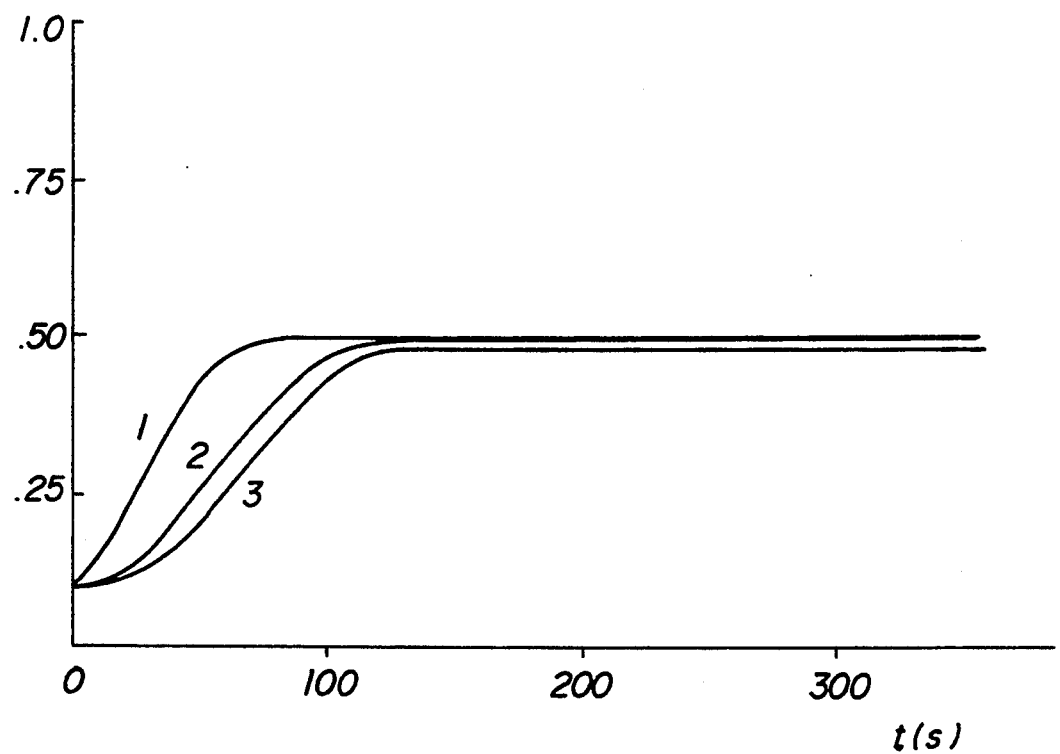
FIG. 3 shows the influence of the thickness of the protective layer on the retention time.

This experiment was carried out as described in example 2. Only the solids content of solution 2 was varied which after drying results in a corresponding variation in the layer thickness of the dry film due to the constant layer thickness when the solution is applied. FIG. 3 clearly shows that the retention time can be varied by the thickness of the layer.

Curve 1: 10% PVP 360, 1% PEG 400
Curve 2: 17% PVP 360, 1.7% PEG 400
Curve 3: 20% PVP 360, 2% PEG 400

EXAMPLE 4

Dissolution Kinetics with Two Discrete Stirring Intervals

Figure 4:
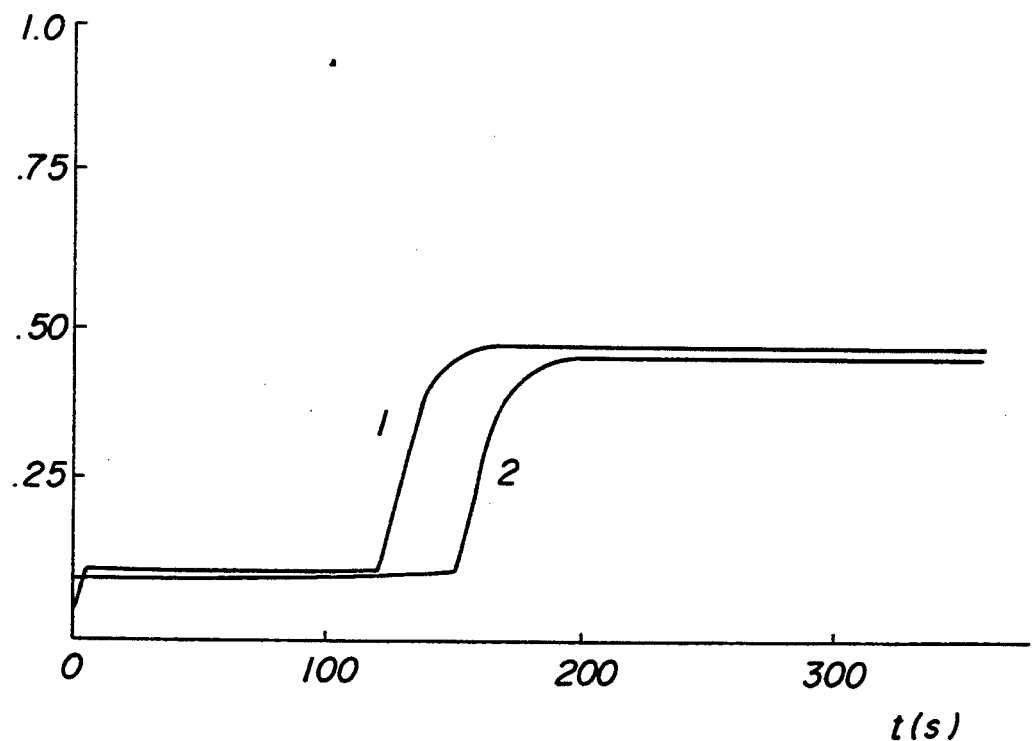
FIG. 4 shows the dissolution kinetics with two discrete stirring intervals.

The experiment was carried out as in example 3, curve 2 with the only difference that a stirrer was switched on from the first to the fifth second and then switched off in order to be switched on again from the 125th second (FIG. 4, curve 1) or 155th second (FIG. 4, curve 2). By switching the stirrer off it is possible to almost completely prevent the release of dye during the entire retarding interval but at the same time a considerably greater jump in the release is achieved. In this way it is possible to vary the retarding interval within wide limits.

EXAMPLE 5

Pancreas α-Amylase Test

An enzymatic colour test was carried out to determine pancreas α-amylase (Boehringer Mannheim GmbH, Order No. 1105 477). In this test the salivary α-amylase which is present in about the same proportion in the sample liquid (serum) is inhibited in a prereaction by reaction with two specific antibodies. In this case it is critical that the binding of these antibodies is only effective, i.e. occurs rapidly, when no substrate for α-amylase is present at the same time in the solution since this competitively inhibits the antibody binding. As a consequence it is necessary to retard the addition or release of the substrate.

A solution of the substrate (19 mmol/14,6-ethylidene-G₇PNP, 105 mmol/l Hepes buffer pH 7.1, 52.5 mmol/l NaCl, 10.5 mmol/l MgCl₂) was firstly added dropwise to the bottom of the reaction vessel (cuvette) and allowed to dry. Then 70 μl of a 5% solution of PVP 360 in propanol was added to the cuvette and again dried. As a result the entire inner surface of the cuvette, i.e. also the optical windows, was coated with a PVP film. The remaining substances necessary for the test procedure were subsequently in turn added dropwise to the bottom of the cuvette in a suitable solution (e.g. 29 U per ml α-glucosidase, 44 g per ml inhibitory monoclonal antibody, 105 mmol/l Hepes buffer pH 7.1, 52.5 mmol/l NaCl, 10.5 mmol/l MgCl₂) and dried. 70 μl pre-diluted sample liquid was added to the cuvette prepared in this manner, stirred for 5 seconds and then stirred again from the 180th to the 330th second. The substrate conversion by -amylase was concurrently monitored photometrically at a measuring wavelength of 415 nm. During the first 5 seconds of the reaction all substances not covered by the protective layer (α-glucosidase, antibody) were dissolved and the pre-reaction began. The increase in signal up to the 180th second is due to a slight swelling of the protective layer and thus to an accompanying change in the optical properties of the PVP film which is located on the optical windows (comparative experiment without reagents). During the second mixing interval the already partially swollen film is completely mixed thus dissolving the substrate. Subsequently the cleavage of the substrate catalysed by α-amylase could proceed.

Test principle:

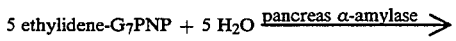

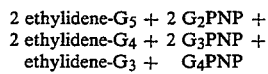

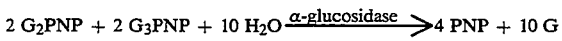

(PNP ≃ p-nitrophenol, G ≃ glucose)

Figure 5:
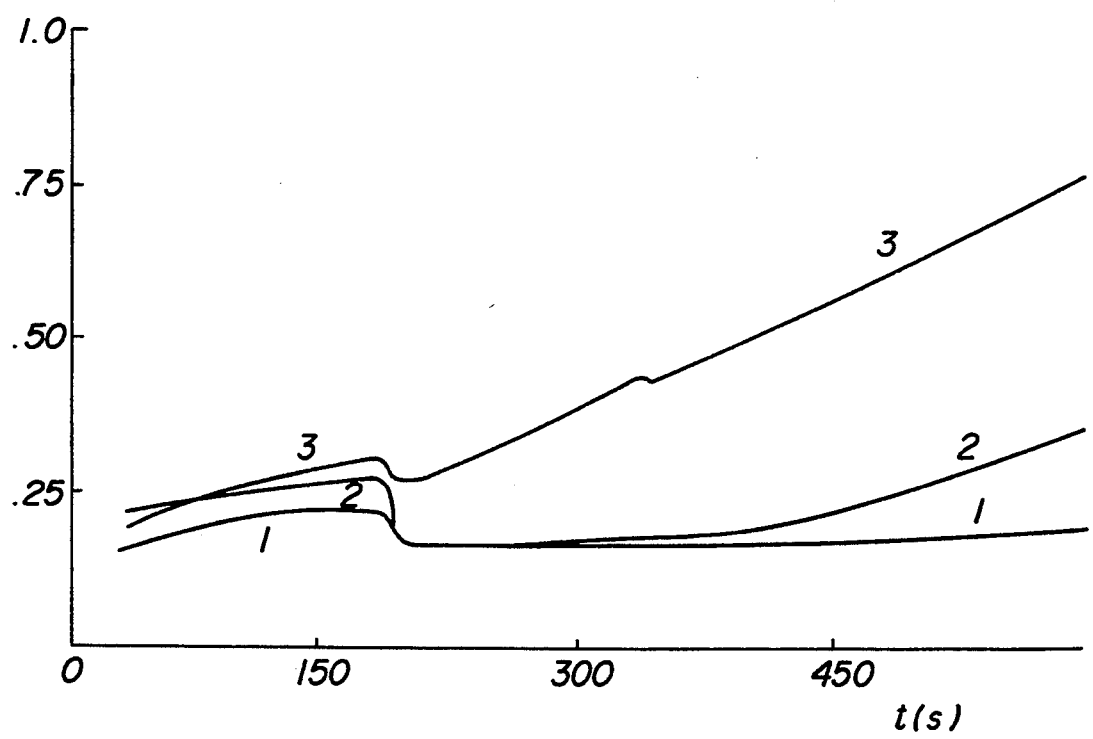
FIG. 5 shows the result of a pancreas α-amylase test when the method according to the invention is carried out.

The result of this experiment is shown in FIG. 5. In curve 1 a pure preparation of salivary amylase (2000 U per l) was used as the sample. One can no longer observe any activity whatsoever. The inhibition by the antibodies was complete. The comparative experiment (curve 2) shows that this is not the case when a release of the substrate occurs during the pre-reaction period. In this case 2000 U/l salivary amylase was again added after 360 seconds which, as can be seen in the figure, is fully active since it no longer adequately inhibited by the antibodies due to the presence of the substrate. Curve 3 shows the reaction time course when a pure preparation of pancreas α-amylase (2000 U/I) is used.

I claim:

1. Method for the determination of an analyte in a sample liquid by a reaction proceeding in several steps which are separated from one another in time, wherein the sample liquid containing the analyte is added to a reaction vessel which contains at least two reagents required to carry out the determination reaction in a form which is readily soluble in the sample liquid and spatially separated from one another wherein a first reagent intended for the first reaction step is in a form which is soluble without delay in the sample liquid while a second reagent intended for the second reaction step and, if desired, further reagents are separated from one another and from the first reagent and are protected from an immediate contact with the sample liquid by protective layers wherein the protective layers are designed in such a way that they enable delayed contact between the sample liquid containing the analyte and the reagent located under the respective protective layer so that a reaction of the analyte with the reagents can take place in several steps which are separated from one another in time and so that the analyte can be determined after completion of the reaction in a homogeneous liquid phase.

2. Method as claimed in claim 1, wherein the protective layers are designed in such a way that they can be made permeable to the sample liquid by the action of the sample liquid or/and by the action of external physical-chemical agents.

3. Method as claimed in claim 2, wherein the protective layers can only be made permeable by interaction with the sample liquid.

4. Method as claimed in claim 3, wherein the protective layers contain a water-soluble polymer.

5. Method as claimed in claim 4, wherein the polymer is a modified cellulose, a gelatin, a polyvinyl alcohol, a polyvinylpyrrolidone, a polyacrylamide or a mixture thereof.

6. Method as claimed in claim 2, wherein the protective layers can only be made permeable by the additional action of external physical-chemical agents.

7. Method as claimed in claim 2 wherein the action of external physical-chemical agents includes the application of heat or radiation or combination thereof.

8. Method as claimed in claim 7, wherein the protective layers contain a photolabile or thermolabile polymer or a mixture thereof.

9. Method as claimed in claim 8, wherein the polymer is a triazene or a pentazadiene polymer.

10. Method as claimed in-one of the claim 2 wherein the protective layers can be made permeable to the sample liquid by an at least partial dissolution.

11. Method as claimed in claim 1 wherein the sample liquid, after addition to the reaction vessel, is mixed with a mixing agent until the first reagent is intimately mixed with the sample, the mixing agent is switched off until the time at which a release of the second reagent is desired, the mixing agent is switched on again until the second reagent has been adequately mixed and if desired the procedure is carried out analogously for further reagents.

12. Method as claimed in claim 11, wherein the mixing is carried out by ultrasonic treatment.

13. Method as claimed in claim 11, wherein the mixing is carried out by a stirrer immersed in the sample liquid.

14. Method as claimed in claim 4 wherein the polymer forming the protective layers is applied from an organic solution in which the reagents located under it are themselves not soluble.

15. Reaction vessel for the determination of an analyte present in a sample liquid by a reaction proceeding in several steps which are separated from one another in time, wherein it contains at least two reagents required to carry out the determination reaction that are in a form which is readily soluble in the sample liquid and are spatially separated from one another, wherein a first reagent intended for the first reaction step is in a form which is soluble without delay in the sample liquid, while a second reagent intended for the second reaction step and if desired further reagents are separated from one another and from the first reagent and are protected from an immediate contact with the sample liquid by protective layers wherein the protective layers are designed in such a way that they enable a delayed contact between the sample liquid containing the analyte and the reagent located under the respective protective layer so that a reaction of the analyte with the reagents can take place in several steps which are separated from one another in time.

16. Reaction vessel as claimed in claim 15, wherein the protective layers are designed in such a way that they can be made permeable to the sample liquid by the action of the sample liquid or by the action of external physical-chemical agents.

17. Reaction vessel as claimed in claim 15, wherein the protective layers can only be made permeable by interaction with the sample liquid.

18. Reaction vessel as claimed in claim 17, wherein the protective layers contain a water-soluble polymer.

19. Reaction vessel as claimed in claim 18, wherein the polymer is a modified cellulose, a gelatin, a polyvinyl alcohol, a polyvinylpyrrolidone, a polyacrylamide or a mixture thereof.

20. Reaction vessel as claimed in claim 16, wherein the action of external physical-chemical agents includes the application of heat or radiation or combination thereof.

21. Reaction vessel as claimed in claim 20, wherein the protective layers contain a photolabile or thermolabile polymer or a mixture thereof.

22. Reaction vessel as claimed in claim 21, wherein the polymer is a triazene or a pentazadiene polymer.

23. Reaction vessel as claimed in claim 15 wherein the protective layers can be made permeable to the sample liquid by an at least partial dissolution.

24. Reaction vessel as claimed in claim 15 wherein the reaction vessel is a cuvette type of test carrier with at least two optically transparent sides.

25. Reaction vessel as claimed in claim 15 wherein the reaction vessel is intended to receive 10 $\mu$l to 5 ml sample liquid.

26. Method as claimed in claim 1, wherein the protective layers are designed in such a way that they can be made permeable to the sample liquid by the action of the sample liquid and the action of external physical-chemical.

27. Method as claimed in claim 16, wherein the protective layers are designed in such a way that they can be made permeable to the sample liquid by the action of the sample liquid and the action of external physical-chemical agents.

* * * * *